United States Patent [19]

Häberlein et al.

[11] 4,129,553

[45] Dec. 12, 1978

[54] ORGANIC PHOSPHITES AND THEIR USE AS STABILIZERS

[75] Inventors: Harald Häberlein; Herbert Nies; Franz Scheidl, all of Gersthofen, Fed. Rep. of Germany

[73] Assignee: Hoechst Aktiengesellschaft, Frankfurt am Main, Fed. Rep. of Germany

[21] Appl. No.: 799,277

[22] Filed: May 23, 1977

[30] Foreign Application Priority Data

May 28, 1976 [DE] Fed. Rep. of Germany ....... 2623985

[51] Int. Cl.² .................. C07F 9/02; C08K 5/36; C08K 5/10; C08K 5/06
[52] U.S. Cl. .............. 260/45.85 R; 260/45.8 A; 260/45.95 L; 260/403; 260/948; 260/949; 260/950; 260/951; 260/952; 260/953
[58] Field of Search ............. 260/399, 403, 951, 952, 260/950, 949, 948, 45.85 R, 953, 45.95 G, 45.7 PH, 45.7 PS, 45.95 L, 45.8 A

[56] References Cited

U.S. PATENT DOCUMENTS

| | | | |
|---|---|---|---|
| 2,711,401 | 6/1955 | Lally | 260/45.75 R |
| 3,055,861 | 9/1962 | Hersh et al. | 260/953 |
| 3,396,130 | 8/1968 | Leistner et al. | 260/952 |
| 3,933,733 | 5/1974 | Kimura et al. | 260/950 |

*Primary Examiner*—V. P. Hoke
*Attorney, Agent, or Firm*—Connolly and Hutz

[57] ABSTRACT

The present invention is related to novel phosphites, their use as stabilizers for organic polymers, furthermore to stabilizer compositions containing these novel phosphites as well as the organic polymers being stabilized therewith.

The novel phosphites have a good stabilization effect, especially in combination with known stabilizers, and they are substantially stable against hydrolytical influence. Their volatility and tendency to exudation are minimal.

6 Claims, No Drawings

ORGANIC PHOSPHITES AND THEIR USE AS STABILIZERS

Our copending application Ser. No. 689.811 which is incorporated herewith by reference, describes novel phosphites of the formula

wherein A, B and C are identical or different organic radicals, at least one of which has the structure

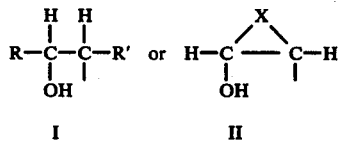

wherein R and R', which may be the same or different, each represents a hydrogen atom, an aryl or cycloalkyl group or an alkyl radical having from 1 to 60 carbon atoms, and wherein the sum of the carbon atoms included in R and R' does not exceed 60, and wherein X represents a straight-chain saturated or unsaturated alkylene radical having from 3 to 10 carbon atoms, while optionally remaining radicals B and C are aryl or cycloalkyl groups or alkyl groups having from 1 to 60 carbon atoms, and wherein the total number of carbon atoms included in the radicals A, B and C is at least 10. Furthermore, there is indicated that the novel phosphites may be used as stabilizers for organic polymers.

There has now been found that organic phosphites of the above formula, wherein the substituent R' in the radical (I) standing for A, B or C is hydrogen and the substituent R has the structure

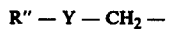

wherein Y stands for —O—, —S— or

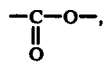

and R" is a phenyl or naphthyl radical optionally substituted by alkyl or isoalkyl groups or by halogen, or a cycloalkyl group having from 5 to 12 ring carbon atoms, or an alkyl chain having from 1 to 60 carbon atoms, optionally interrupted by ether, thioether, carboxylic acid ester groups and/or —C═C double bonds, and optionally substituted by an (alkyl)substituted phenyl or naphthyl radical, are excellent stabilizers for plastic compositions.

The present invention provides therefore the above, hitherto unknown, organic phosphites, their use as stabilizers for organic polymers, stabilizer combinations containing these phosphites, and organic polymers so stabilized.

The novel phosphites are far superior to the known organic phosphites with respect to their stabilizing effect. A further advantage resides in the fact that those representatives of the novel phosphites which, at room temperature, are present in the form of solid substances impart an improved thermostability to the plastic shaped articles processed with their aid as compared to the thermostability attained with the use of known liquid products. Also, the use of phosphites of the present invention reduces substantially tarnishing of the processing machines and the formation of grooves on the shaped articles being produced. Additional useful properties of phosphites of the present invention are the general lack of smell, the practical absence of volatility and the lack of tendency to exudation.

The phosphites of the present invention may be obtained according to known methods by transesterification of tri-lower alkyl-phosphites or of triphenyl phosphites with di-hydroxy compounds of the structure

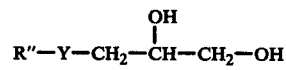

in which ester interchange the primary, more reactive, hydroxyl group reacts practically exclusively. The dihydroxy compounds may be of industrial-grade quality; thus, for example, industrial-grade glycerol monostearate or mono-oleate may be used. When mixtures of dihydroxy and high-boiling monohydroxy compounds, for example lauryl alcohol, stearyl alcohol or nonylphenol, are used for the ester interchange, a maximum 2 mols only of monohydroxy compound per mol of trilower alkylphosphite should be used, since at least one of the radicals A, B and C of the general formula must have the structure of the formula III according to the invention.

The novel phosphites are generally and preferably solid white products some of which have a wax-like character. Some are still liquid at room temperature. Most interesting are the first ones, having flow/droppoints of from 35° to 100° C., since in addition to their stabilization effect, they influence favorably the properties of the products made of polymer molding compositions containing such wax-like phosphites.

In the phosphites of the formula

A, B and C are identical or different organic radicals; one at least of these radicals must have a structure of the formula

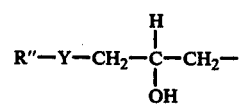

In the case where the radical A alone has one of these structures, B and C may be alkyl groups having from 1 to 60, preferably 1 to 30, carbon atoms, and/or aryl groups having from 6 to 12 carbon atoms and/or cycloalkyl groups having from 5 to 12 carbon atoms, preferably 5 or 6 carbon atoms. The aryl group may optionally be substituted by alkyl or alkoxyl radicals having preferably 1 to 6 carbon atoms. In the case where A and B have the structure III, C is one of the radicals just cited.

The symbol Y used in the formula III stands for —O—, —S—, or

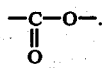

R" represents a phenyl or naphthyl group optionally substituted by 1 to 3 alkyl or isoalkyl groups having from 1 to 12, preferably 1 to 9, carbon atoms, or by up to 5 halogen atoms, preferably chlorine atoms, or an unsubstituted or substituted cycloalkyl group having from 5 to 12, preferably 5 or 6, ring carbon atoms. Examples are the phenyl, tolyl, xylyl, tert.-butyl-phenyl, chlorophenyl, nonylphenyl, naphthyl, cyclopentyl, cyclohexyl, cycloheptyl, cyclooctyl or cyclododecyl group. R" may also stand for a linear or branched alkyl radical having from 1 to 60, preferably 8 to 40, carbon atoms; this alkyl radical optionally containing ether, thioether, carboxylic acid ester groups and/or —C=C double bonds, and/or phenyl or naphthyl radicals optionally substituted for their part by 1 to 3 alkyl or isoalkyl groups having from 1 to 12, preferably 1 to 9, carbon atoms. Examples are the octyl, decyl, dodecyl, tetradecyl, hexadecyl, octadecyl, eicosyl, docosyl, tetracosyl, hexacosyl, octacosyl, triacontyl, dotriacontyl, tetratriacontyl, hexatriacontyl, octatriacontyl, tetracontyl, dotetracontyl, behenyl or mantanyl radicals and radicals of the following structures:

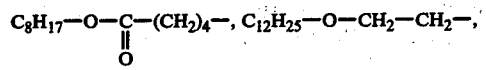

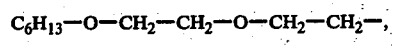

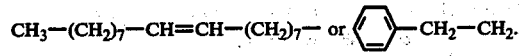

Preferred radicals R" of the formula III are linear, saturated or unsaturated alkyl radicals having from 6 to 58, preferably 9 to 40, and especially 11 to 36, carbon atoms. The phosphites are furthermore characterized in that the total number of all carbon atoms contained in the radicals A, B and C is at least 10, preferably at least 16.

Some especially typical representatives of the novel phosphites are listed below; the invention, however, not being limited to the cited substances:
Tris-(3-stearoyl-2-hydroxy-propyl)phosphite

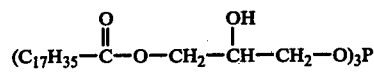

Ethyl-bis-(3-palmitoyl-2-hydroxy-propyl)phosphite

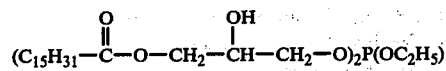

Stearyl-bis-(3-palmitoyl-2-hydroxy-propyl)phosphite

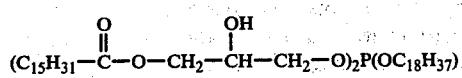

Phenyl-bis-(3-dodecyloxy-2-hydroxy-propyl)phosphite

Dilauryl-(3-oleoyl-2-hydroxy-propyl)phosphite

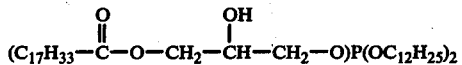

Tris-(3-phenoxy-2-hydroxy-propyl)phosphite

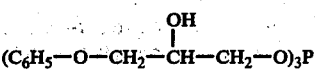

Diethyl-(3-montanoyl-2-hydroxy-propyl)phosphite

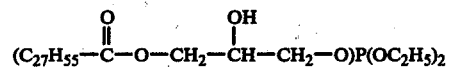

Palmityl-bis-(3-phenylethoxy-2-hydroxy-propyl)-phosphite

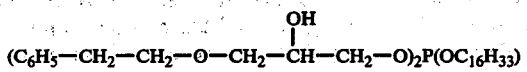

Phenyl-bis-(3-dodecylthio-2-hydroxy-propyl)phosphite

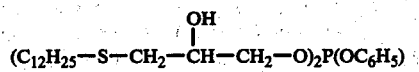

Stearyl-bis-(3-nonylphenoxy-2-hydroxy-propyl)-phosphite

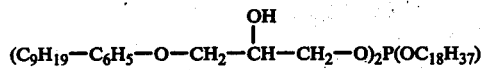

Butyl-bis-(3-octyldiglycoxy-2-hydroxy-propyl)phosphite

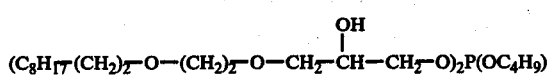

The novel phosphites may be used also in mixture with each other, optionally together with other generally known stabilizers. There may be added to the compositions to be stabilized further stabilizing auxiliaries, antioxidants and UV stabilizing compounds. The amounts of phosphite of the invention to be used is from 0.01 to 10, preferably 0.05 to 3, parts by weight, relative to 100 parts by weight of polymer to be stabilized.

When chlorinated polymers, such, for example, as chloropolyethylene, hard and soft polyvinyl chloride, polyvinylidene chloride, polyvinyl chloroacetate and vinyl chloride-α-olefin-copolymers are processed, a substantially improved stability to heat and to light is achieved by adding the novel phosphites, in the presence of metal compounds known as stabilizers, indoles substituted in the 2-position, preferably 2-phenylindole, epoxide stabilizers and/or possibly polyhydric alcohols.

Suitable metal compounds known as stabilizers are, for example, Ca, Ba, Sr, Zn, Cd, Mg, Al and Pb soaps of aliphatic carboxylic acids or oxycarboxylic acids having from 8 to 32 carbon atoms, preferably from 8 to 24 carbon atoms, salts of these metals with aromatic carboxylic acids of preferably from 7 to 12 carbon atoms, e.g. benzoates, salicylates as well as (alkyl)phenolates of these metals, the alkyl radical having from 1 to 12, preferably from 1 to 6, carbon atoms. This range of compounds also includes organo-tin compounds, e.g. dialkyltin-thioglycolates and carboxylates as well as — optionally — neutral and basic lead salts of inorganic acids such, for example, as sulfuric acid and phosphorous acid.

Known epoxide stabilizers are, for example, higher epoxidized fatty acids such, for example, as epoxidized soybean oil, tall oil or linseed oil, epoxidized butyl oleate and higher epoxyalkanes.

Polyhydric alcohols are, for example, pentaerythritol, trimethylol propane, sorbitol or mannitol, i.e., preferably alcohols having from 5 to 6 carbon atoms and from 3 to 6 OH groups.

Stabilizers of this kind, e.g. metal compounds, epoxides and polyhydric alcohols are described, for example, in J. Voigt "Stabilisierung der Kunststoffe gegen Licht und Wärme", Springer-Verlag, Berlin-Heidelberg-New York (1966).

A very efficient stabilizer composition for processing halogenated polymer molding compositions consists, for example, of from 0.01 to 10 parts by weight of a phosphite of the invention, 0.1 to 10 parts by weight of a metal compound known as stabilizer, 0.1 to 10 parts by weight of a known epoxide stabilizer and 0 to 1 part by weight of a polyhydric alcohol.

The novel phosphites display also an excellent efficiency for stabilizing polymers or copolymers of olefins free from halogen. The stability of, for example, polypropylene to heat and to light is considerably improved by the addition of the novel phosphites, especially in admixture with phenolic and/or sulfidic stabilizers.

By phenolic and sulfidic stabilizers there are to be understood the generally known stabilizers against heat and light which are used in the processing of plastics, for example 3,5-ditertiarybutyl-4-hydroxyphenyl-propionic acid ester, 2,6-ditertiarybutyl-p-cresol, alkylidene-bis-alkyl-phenols, esters of bis-(4'-hydroxy-3'-tertiary-butylphenyl)-butyric acid, thiodipropionic acid ester of fatty alcohols as well as dioctydecyl sulfide or dioctadecyl disulfide; (cf. J. Voigt, "Stabilisierung der Kunststoffe gegen Licht und Warme", Springer-Verlag, Berlin-Heidelberg-New York (1966)).

A synergistically efficient stabilizer composition for polymers or copolymers of olefins free from halogen consists, for example, of from 0.05 to 3 parts by weight of a phosphite according to the invention, from 0.05 to 3 parts by weight of a known phenolic stabilizer and/or of from 0.1 to 3 parts by of a known sulfidic stabilizer. Special stabilizers against ultra-violet rays may also be added to the stabilizer composition in an amount of from 0.1 to 3 parts by weight, if necessary. Known ultra-violet absorbers are, for example, alkoxy-hydroxybenzophenones, hydroxyphenylbenzotriazoles, salicilic acid phenolic ester, benzoic acid hydroxyphenolic ester, benzylidene malonic acid mononitrile ester as well as so-called "quenchers" such, for example, as nickel chelates, hexamethyl-phosphoric acid triamide or — as recently made known — piperidine stabilizers.

Stabilizer compositions of the phosphites according to the invention and known stabilizers not only improve the stability of polyolefins, chloropolyolefins and chlorinated vinylpolymers, but impart also an improved stability to polyesters, polyamides, polyacrylonitrile, polycarbonates, polysiloxanes, polyethers, polyurethanes and others.

The following Examples illustrate the invention and show the advantages of the novel phosphites.

EXAMPLE 1

A 1 liter-four-necked flask, equipped with an agitating device, an internal thermometer, gas inlet and descending cooler, was rinsed with nitrogen and subsequently charged with 516 g (1.5 mol) of octadecoxypropanediol-1,2 and 124,5 g (0.5 mol) of freshly distilled triethyl phosphite. The contents of the flask were heated to 115°–120° C. in the course of 20–30 minutes in a weak nitrogen current, while stirring, ethanol then starting to separate at an internal temperature of about 110° C. Within a further 3–5 hours, while stirring was continued, the temperature of the reaction mixture was slowly increased from 120° C. to a final temperature of 160° C. 66 g of ethanol were distilled off during this period of time. Agitation was then continued for another hour in a water jet vacuum of 10–20 mm at the unaltered temperature of 160° C., in order to remove possible volatile components. After this period, 3.4 g of a liquid consisting of 2.0 g of triethyl phosphite and a further 1.4 g of ethanol were found in a cooling trap inserted between the described apparatus and the water jet pump.

Thus a total quantity of 67.4 g (97.6% of the theoretical yield) of ethanol was separated.

After cooling of the limpid, slightly yellowish melt 566 g (99% of the theoretical yield) of ethyl-bis(3-octadecoxy-2-hydroxy-propyl)phosphite were obtained in the form of a wax having a flow/drop point of 62°–63° C. (determined according to DGF M III 3 (57)), containing 3.9% of phosphorus, and having a molecular weight of 746. The calculated values for a compound of formula $C_{44}H_{91}O_7P$ are 4.1% P and a molecular weight of 762.

EXAMPLES 2 to 10

According to the method described in Example 1, further representatives of the novel phosphites (Examples 2 to 9) and, for a comparison, ethyl-bis(octadecyl) phosphite (Example 10) were synthetized. The following Table shows the special preparation characteristics and the analytical characterization of the products obtained.

In Example 9, a mixture of 1 mol of stearyl alcohol and 1 mol of 3-dodecoxy-propanediol-1,2 was reacted.

| | starting materials | | |
|---|---|---|---|
| Example No. | formula of the diol | Amount in mols and grams | Phosphite used | Amount in mols and grams |
| 2 | $C_{12}H_{25}$—S—$CH_2$—CH(OH)—$CH_2$(OH) | 1.5 / 414 | TEP[2)] | 0.75 / 124.5 |

-continued

| Example No. | starting materials formula of the diol | Amount in mols and grams | Phosphite used | Amount in mols and grams |
|---|---|---|---|---|
| 3 | ⟨phenyl⟩—O—CH$_2$—CH(OH)—CH$_2$(OH) | 1.5 / 252 | TEP | 0.75 / 124.5 |
| 4 | C$_{17}$H$_{35}$—CO$_2$—CH$_2$—CH(OH)—CH$_2$(OH) | 1.5 / 537 | TEP | 1.5 / 249 |
| 5 | C$_{17}$H$_{35}$—CO$_2$—CH$_2$—CH(OH)—CH$_2$(OH) | 1.5 / 537 | TEP | 0.75 / 124.5 |
| 6 | C$_{17}$H$_{35}$—CO$_2$—CH$_2$—CH(OH)—CH$_2$(OH) | 1.5 / 537 | TEP | 0.5 / 83 |
| 7 | C$_{17}$H$_{35}$—CO$_2$—CH$_2$—CH(OH)—CH$_2$(OH) | 1.5 / 537 | TPP[3] | 0.75 / 232.5 |
| 8 | ind.-grade GMS[1] | [4] / 510 | TEP | 0.75 / 124.5 |
| 9 | C$_{12}$H$_{25}$—O—CH$_2$—CH(OH)—CH$_2$(OH) C$_{18}$H$_{37}$OH | 1 / 260 1 / 270 | TEP | 1 / 166 |
| 10 (Comp.) | C$_{18}$H$_{37}$OH | 1 / 270 | TEP | 0.5 / 83 |

[1] GMS = industrial-grade glycerol monostearate composed of about 55% glycerol monostearate, 35% glycerol distearate and 10% glycerol tristearate of the hydroxy number 242
[2] TEP = triethyl phosphite
[3] TPP = triphenyl phosphite,
[4] 2.2 equivalent OH groups

| Example No. | Products of the process Phosphite obtained | P % b.w. calc. | P % b.w. found | mol.wt. calc. | mol.wt. found | flow/drop point °C |
|---|---|---|---|---|---|---|
| 2 | Ethyl-bis-(3-dodecylthio-2-hydroxy-propyl) phosphite | 4.9 | 4.6 | 626 | 595 | liquid |
| 3 | Ethyl-bis-(3-phenoxy-2-hydroxy-propyl) phosphite | 7.6 | 7.7 | 410 | 423 | 30/31 |
| 4 | Diethyl-(3-stearoyl-2-hydroxy-propyl) phosphite | 6.5 | 6.1 | 478 | 452 | 48/49 |
| 5 | Ethyl-bis-(3-stearoyl-2-hydroxy-propyl) phosphite | 3.9 | 4.0 | 790 | 756 | 59/60 |
| 6 | Tris-(3-stearoyl-2-hydroxy-propyl) phosphite | 2.8 | 2.6 | 1102 | 1049 | 62/63 |
| 7 | Phenyl-bis-(3-stearoyl-2-hydroxy-propyl) phosphite | 3.7 | 3.4 | 838 | 851 | 60/61 |
| 8 | — | 4.1 | 4.0 | — | — | 45/45.5 |
| 9 | Ethyl-octadecyl-(3-dodecyloxy-2-hydroxy-propyl) phosphite | 5.1 | 5.0 | 604 | 577 | 43/44 |
| 10 (Comp.) | Ethyl-bis-(octadecyl) phosphite | 4.9 | 4.8 | 638 | 609 | 40.5/41.5 |

EXAMPLES 11 to 38

These Examples illustrate the stabilizing effect of phosphites of the present invention on the processing of polyvinyl chloride. The dynamic thermostability (Examples 11 to 24) and the static thermostability (Examples 25 to 38) were determined. The specified parts are parts by weight.

For each of a number of phosphites of the present invention, 100 parts of a mass-polyvinyl chloride having a K-value of 60 were mixed thoroughly with 0.2 parts of 2-phenylindole, 3 parts of epoxidized soybean oil, 0.25 parts of a complex calcium/zinc stabilizer consisting of 42 weight % of calcium stearate, 30 weight % of zinc stearate, 22 weight % of pentaerythrite and 6 weight % of 2,6-di-t-butyl-4-methylphenol, 0.2 part of a montanic acid ester (acid number 18, saponification number 154), 0.3 part of stearyl stearate, 0.5 part of glycerol monostearate, and 0.5 part of the phosphite.

In order to determine the dynamic thermostability each mixture was applied on to a laboratory-scale twin-roller device heated to 180° C., and rolled-out to a rough sheet within one minute at 20 rpm. At intervals of 10 minutes, spot samples were picked of these sheets, and their color shades compared with an internal color chart. The various tests were run until the rough sheet had taken up a dark-brown to black shade.

In order to determine the static thermostability, a rough sheet was first prepared from each mixture according to the description given above, and this sheet was rolled out on the twin-roller device at 180° C. for another 10 minutes' period. The sheet was then peeled off the roller and little plates of about 0.5 mm thickness and a diameter of 30 mm blanked therefrom. These specimens were wrapped in an aluminium sheet and tempered at 180° C. in a heating cabinet with internal air circulation. One specimen was selected every 10 minutes and its color shade compared with the color chart. The figures employed in the color chart have the following meaning:

1 = clear as water
2 = slightly yellowish
3 = distinctly yellow tint
4 = dark yellow-brown shade
5 = dark brown to black As demonstrated by the following Tables, as far as dynamic and static thermostability are concerned, the polyvinyl chloride stabilized by organic phosphites of the present invention is clearly superior in comparison to polyvinyl chloride stabilized with known phosphites and with mixtures free from phosphites.

Dynamic thermostability

| Example No. | Phosphite acc. to Example | Discoloration of rough sheet at a laminating time of | | | | | | | |
|---|---|---|---|---|---|---|---|---|---|
| | | 10' | 20' | 30' | 40' | 50' | 60' | 70' | 80' |
| | | to color number | | | | | | | |
| 11 | 1 | 1 | 2 | 2–3 | 2–3 | 3 | 5 | — | — |
| 12 | 2 | 1 | 2 | 2–3 | 3 | 3 | 3–4 | 5 | — |
| 13 | 3 | 1 | 2 | 2–3 | 2–3 | 3 | 3 | 5 | — |
| 14 | 4 | 1 | 1–2 | 2 | 3 | 3 | 3 | 5 | — |
| 15 | 5 | 1 | 1–2 | 2 | 2–3 | 3 | 3 | 5 | — |
| 16 | 6 | 1 | 1–2 | 2 | 2–3 | 3 | 3 | 3–4 | 5 |
| 17 | 7 | 1 | 1–2 | 2 | 2 | 3 | 3 | 5 | — |
| 18 | 8 | 1 | 1–2 | 2 | 2–3 | 3 | 3 | 5 | — |
| 19 | 9 | 1 | 2 | 2 | 2 | 3 | 3 | 5 | — |
| 20 (comp.) | 10 | 1 | 1–2 | 2 | 3 | 5 | — | — | — |
| 21 (comp.) | Triphenyl phosphite | 1 | 2 | 2–3 | 5 | — | — | — | — |
| 22 (comp.) | Trisnonyl-phenyl phosphite | 1 | 2 | 2–3 | 5 | — | — | — | — |
| 23 (comp.) | Diphenyl-isooctyl phosphite | 1 | 2–3 | 3 | 5 | — | — | — | — |
| 24 (comp.) | none | 2 | 2–3 | 3–4 | 5 | — | — | — | — |

Static thermostability

| Example No. | Phosphite acc. to Example | Discoloration of rough sheet in drying cabinet at a tempering time of | | | | | | | | |
|---|---|---|---|---|---|---|---|---|---|---|
| | | 0' | 20' | 30' | 40' | 50' | 60' | 70' | 80' | 0' |
| | | to color number | | | | | | | | |
| 25 | 1 | 1 | 2 | 2 | 2–3 | 3 | 3 | 3 | 5 | — |
| 26 | 2 | 1 | 2 | 2 | 2–3 | 3 | 3 | 5 | — | — |
| 27 | 3 | 1 | 2 | 2 | 2 | 3 | 3 | 3 | 5 | — |
| 28 | 4 | 1 | 2 | 2 | 2–3 | 3 | 3 | 3–4 | 5 | — |
| 29 | 5 | 1 | 1–2 | 2 | 2–3 | 3 | 3 | 3–4 | 5 | — |
| 30 | 6 | 1 | 1–2 | 2 | 2–3 | 3 | 3 | 3 | 3–4 | 5 |
| 31 | 7 | 1 | 1–2 | 2 | 2–3 | 3 | 3 | 3–4 | 5 | — |
| 32 | 8 | 1 | 2 | 2–3 | 2–3 | 3 | 3 | 3–4 | 5 | — |
| 33 | 9 | 1 | 2 | 2–3 | 2–3 | 3 | 3 | 3–4 | 5 | — |
| 34 (comp.) | 10 | 1 | 2 | 2 | 2–3 | 3 | 3–4 | 5 | — | — |
| 35 (comp.) | Triphenyl phosphite | 1 | 1–2 | 2 | 2–3 | 3 | 5 | — | — | — |
| 36 (comp.) | Trisnonyl-phenyl phosphite | 1 | 2 | 2–3 | 3 | 5 | — | — | — | — |
| 37 (comp.) | Diphenyl-isooctyl phosphite | 1 | 2 | 2 | 2 | 3 | 3–4 | 5 | — | — |
| 38 (comp.) | none | 1 | 2–3 | 2–3 | 2–3 | 3–4 | 5 | — | — | — |

EXAMPLES 39 to 42

These Examples show that the addition of the phosphites of the present invention to polypropylene improves considerably its stability to light and against alterations due to heat.

Powdery mixtures consisting each of
100 parts by weight of unstabilized polypropylene

[$i_{5(230° C.)}$ about 8]

0.15 part by weight of octadecyl-3-(3',5'-di-tert.-butyl-4'-hydroxyphenyl)-propionate
and
0.10 part by weight of the phosphites prepared according to Examples 1, 6 and 9 were injection-molded on an injection molding machine to yield test plates measuring 60 × 60 × 1 mm. Test specimens were blanked from these plates.

The stability to light was determined by means of the Xeno-test device, type 150, produced by Messrs. Hanau Quarzlampen GmbH with the filter combination 6 IR + 1 UV as per DIN 53 387. (DIN = German Industrial Standard). The time of exposure to light, i.e. the period of time after which the absolute elongation at break had decreased to 10% was measured in hours.

The resistance to alteration under heat of injection molded test samples was measured approximately to the procedure described by DIN 53 383 by storing the specimens at an air temperature of 140° C. until total embrittlement.

The following Table demonstrates the good light and heat stabilizing effect of the phosphites in polypropylene.

Stability to light and alteration due to heat

| Example No. | Phosphite acc. to Example | Time of exposure in hours | Stability to alteration due to heat in days |
|---|---|---|---|
| 39 | 1 | 710 | 41 |
| 40 | 6 | 685 | 44 |
| 41 | 9 | 725 | 39 |
| 42 (comp.) | without phosphite | 530 | 21 |

What is claimed is:
1. Phosphites of the formula

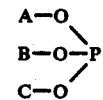

wherein A, B and C are identical or different radicals, and at least one is a member of the structure

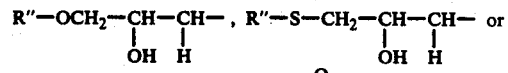

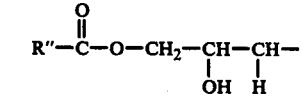

wherein R" is a phenyl- or naphthyl group or a cycloalkyl group having from 5 to 12 ring carbon atoms or an alkyl chain having from 1 to 60 carbon atoms, and any radicals of A, B and C remaining are aryl groups having from 6 to 12 carbon atoms or cycloalkyl groups having from 5 to 12 carbon atoms or alkyl groups having from 1 to 60 carbon atoms, the total sum of carbon atoms contained in the radicals A, B and C being at least 10.

2. Stabilizer combination for chlorinated polyolefins and chlorine containing vinyl homo- and copolymers, consisting of 0.01 to 10 parts by weight of a phosphite as claimed in claim 1, 0.1 to 10 parts by weight of metal compounds known as stabilizers, 0 to 10 parts by weight of a known epoxide stabilizer, and 0 to 1 part by weight of a known polyol.

3. Stabilizer combination for homopolymers or copolymers of halogen-free olefins, consisting of 0.05 to 5 parts by weight of a phosphite as claimed in claim 1, 0.05 to 3 parts by weight of a known phenolic stabilizer and/or 0.1 to 3 parts by weight of a known sulfidic stabilizer, and 0 to 3 parts by weight of a known ultraviolet stabilizer.

4. A process for stabilizing chlorinated polyolefins, chlorine-containing vinyl homo- and copolymers or polymers or copolymers of halogen-free olefins, which comprises adding to the polymer a phosphite of claim 1.

5. The process of claim 4 wherein there is added to the polymer the phosphite of claim 1 in combination with at least one further additive selected from the group consisting of a metal compound stabilizer, an epoxide stabilizer, a phenolic stabilizer, a sulfidic stabilizer, a polyol stabilizer and an ultraviolet stabilizer.

6. Plastic molding compositions containing a phosphite as claimed in claim 1 as stabilizer.

* * * * *